US007361676B2

(12) United States Patent
Iwai et al.

(10) Patent No.: US 7,361,676 B2
(45) Date of Patent: Apr. 22, 2008

(54) SOLID PREPARATION CONTAINING SINGLE CRYSTAL FORM (75) Inventors: Michio Iwai, Osaka (JP); Kazuhiro Nakamura, Yamaguchi (JP); Masahiko Dohi, Tokyo (JP); Hiroko Mochizuki, Yamaguchi (JP); Seiji Mochizuki, Yamaguchi (JP)

(73) Assignee: Teijin Limited, Osaka (JP)

( * ) Notice: Subject to any disclaimer, the term of this patent is extended or adjusted under 35 U.S.C. 154(b) by 346 days.

(21) Appl. No.: 10/503,391

(22) PCT Filed: Mar. 28, 2003

(86) PCT No.: PCT/JP03/03962

§ 371 (c)(1),
(2), (4) Date: Aug. 3, 2004

(87) PCT Pub. No.: WO03/082279

PCT Pub. Date: Oct. 9, 2003

(65) Prior Publication Data

US 2005/0043375 A1 Feb. 24, 2005

(30) Foreign Application Priority Data

Mar. 28, 2002 (JP) ............................. 2002-090889

(51) Int. Cl.
*A61K 31/425* (2006.01)
*C07D 277/00* (2006.01)

(52) U.S. Cl. ..................................... 514/365; 548/201
(58) Field of Classification Search ................ 514/365; 548/201
See application file for complete search history.

(56) References Cited

U.S. PATENT DOCUMENTS 5,614,520 A * 3/1997 Kondo et al. ............. 514/236.8
6,225,474 B1 * 5/2001 Matsumoto et al. ........ 548/201

FOREIGN PATENT DOCUMENTS

| EP | 0513379 A1 | 11/1992 |
| EP | 0779074 A1 | 6/1997 |
| EP | 1 020 454 A1 | 12/1999 |
| EP | 1020454 A1 | 7/2000 |
| WO | WO 92/09279 A1 | 6/1992 |
| WO | WO 99/65885 A1 | 12/1999 |

OTHER PUBLICATIONS

M. Kitamura, et al., Effects of solvent composition and temperature on polymorphism and crystallization behavior of thiazole-derivative, Journal of Crystal Growth, Mar. 2002, vol. 236, No. 4, pp. 676 to 686.

* cited by examiner

*Primary Examiner*—Rei-tsang Shiao
(74) *Attorney, Agent, or Firm*—Sughrue Mion, PLLC (57) ABSTRACT There are provided a solid preparation containing a single crystal of 2-(3-cyano-4-isobutyloxyphenyl)-4-methyl-5-thiazolecarboxylic acid, an excipient and a disintegrating agent, and a method for producing the same.

10 Claims, 5 Drawing Sheets

SOLID PREPARATION CONTAINING SINGLE CRYSTAL FORM

This application is a 371 of PCT/JP03/03962 filed on Mar. 28, 2003.

TECHNICAL FIELD

The present invention relates to a solid preparation of 2-(3-cyano-4-isobutyloxyphenyl)-4-methyl-5-thiazole carboxylic acid for oral administration. More particularly, it relates to a solid preparation comprising 2-(3-cyano-4-isobutyloxyphenyl)-4-methyl-5-thiazole carboxylic acid as a single crystal form, and a method for producing the same.

BACKGROUND ART 2-(3-cyano-4-isobutyloxyphenyl)-4-methyl-5-thiazole-carboxylic acid has a strong activity for inhibiting xanthine oxidase or a uric acid decreasing action, and it is expected to be a therapeutic agent for gout or hyperuricemia, as has been described in International Publication WO92/09279.

In International Publication WO99/65885, there are described following six crystal polymorphs of 2-(3-cyano-4-isobutyloxyphehyl)-4-methyl-5-thiazole carboxylic acid, i.e., a polymorph which shows an X-ray powder diffraction pattern having specific peaks at a reflection angle 2θ, of about 6.62°, 7.18°, 12.80°, 13.26°, 16.48°, 19.58°, 21.92°, 22.68°, 25.84°, 26.70°, 29.16° and 36.70° (crystal A).;

a polymorph which has specific peaks at a reflection angle 2θ of about 6.76°, 8.08°, 9.74°, 11.50°, 12.22°, 13.56°, 15.76°, 16.20°, 17.32°, 19.38°, 21.14°, 21.56°, 23.16°, 24.78°, 25.14°, 25.72°, 26.12°, 26.68°, 27.68° and 29.36° (crystal B);

a polymorph which has specific peaks at a reflection angle 2θ of about 6.62°, 10.82°, 13.36°, 15.52°, 16.74°, 17.40°, 18.00°, 18.70°, 20.16°, 20.62°, 21.90°, 23.50°, 24.78°, 25.18°, 34.08°, 36.72° and 38.04° (crystal C);

a polymorph which has specific peaks at a reflection angle 2θ of about 8.32°, 9.68°, 12.92°, 16.06°, 17.34°, 19.38°, 21.56°, 24.06°, 26.00°, 30.06°, 33.60° and 40.34° (crystal D).; and a polymorph which has specific peaks at a reflection angle 2θ of about 6.86°, 8.36°, 9.60°, 11.76°, 13.74°, 14.60°, 15.94°, 16.74°, 17.56°, 20.00°, 21.26°, 23.72°, 24.78°, 25.14°, 25.74°, 26.06°, 26.64°, 27.92°, 28.60°, 29.66° and 29.98° (crystal G), and an amorphous (also referred to as crystal E).

In said International Publication WO99/65885, it is described that crystals A, C and G are useful in view of retention of a crystal form in long term storage. Among them, crystal A is preferred in view of industrial superiority.

However, the publication is silent about what the industrial superiority means. Further, the publication has no evidence (data) supporting the fact that the crystal A is preferred in view of industrial superiority.

The present inventors investigated this matter and found that, in formulating 2-(3-cyano-4-isobutyloxyphenyl)-4-methyl-5-thiazole carboxylic acid, it is not possible to obtain preparations having no variation in the dissolution profiles of drugs, even if such a crystal form is used as is thought to be most stable in a physical stability test. Further, they found that there is a crystal form that is suitable for preparing preparations, independently from the characteristics of the crystals (including amorphous) of drug substances and have reached the invention.

An object of the invention is, therefore, to provide solid preparations of 2-(3-cyano-4-isobutyloxyphenyl)-4-methyl-5-thiazolecarboxylic acid which is stable and which is little variation in the dissolution profiles.

DISCLOSURE OF THE INVENTION

The invention provides solid preparations containing a single crystal form of 2-(3-cyano-4-isobutyloxyphenyl)-4-methyl-5-thiazolecarboxylic acid, excipients and disintegrating agents.

Further, the invention provides a process for producing solid preparations containing a single crystal form of 2-(3-cyano-4-isobutyloxyphenyl)-4-methyl-5-thiazolecarboxylic acid, excipients and disintegrating agents.

BEST MODE FOR CARRYING OUT THE INVENTION

The single crystal of the 2-(3-cyano-4-isobutyloxyphenyl)-4-methyl-5-thiazolecarboxylic acid (also referred to as the drug substance of the invention) of the invention is that which has a characteristic spectrum when the drug substance is analyzed by a solid NMR or that having specific peaks when analyzed by an X-ray powder diffraction.

The crystal of the invention, i.e., the crystal A of the drug substance of the invention has, when analyzed by a solid $^{15}$N-NMR a, a spectrum having specific signals at 226 ppm, 228 ppm, 276 ppm, and 282 ppm. When analyzed by a solid $^{13}$C-NMR, the crystal A has approximately equivalent doublet peak at 20 ppm.

Further, the crystal of the drug substance of the invention shows an X-ray powder diffraction pattern having specific peaks at a reflection angle 2θ, of about 6.62°, 7.18°, 12.80°, 13.26°, 16.48°, 19.58°, 21.92°, 22.68°, 25.84°, 26.70°, 29.16° and 36.70°.

The crystal of the drug substance of the invention can be produced by the method shown in, for example, International Publication WO 92/09279 and WO 99/65885.

The crystal of the drug substance of the invention is contained in the solid preparation of the invention preferably in an amount of 1 to 50 parts by weight based on 100 parts by weight of the solid preparation.

There are no particular restrictions to the average particle size of the crystal of the drug substance of the invention contained in the solid preparation of the invention. The average particle size is preferably 3 µm or greater and 50 µm or less, when it is determined by an image analysis.

Examples of the excipients for the solid preparation of the invention include lactose, lactose anhydride, crystalline cellulose, corn starch, pregelatinized starch, partly pregelatinized starch, D-mannitol and dibasic calcium phosphate. Particularly the lactose, crystalline cellulose, starches or their combination are preferable. The excipients are contained in an amount of 50 to 98 parts by weight, and more preferably 60 to 95 parts by weight, based on 100 parts by weight of the solid preparation.

Examples of the disintegrating agent for the solid preparation of the invention include carmellose sodium, carmellose calcium, low-substituted hydroxypropyl cellulose, crosscarmellose sodium, carboxymethyl starch sodium and crosspovidone. Particularly the crosscarmellose sodium and partly pregelatinized starch are preferable. The disintegrating agent is contained in an amount of 1 to 25 parts by weight, preferably 1.5 to 20 parts by weight, based on 100 parts by weight of the solid preparation.

There may be added known binders, lubricants, coating agents, plasticizers, diluents, colorants, preservatives, antiseptics or fragrance agents to the solid preparation of the invention to improve the physical properties, appearance, odor, etc. of the preparation.

The binders for the solid preparation of the invention may be those known to the persons in the art. Particularly preferable binders are hydroxypropyl cellulose, hydroxy propylmethyl cellulose, and polyvinyl pyrrolidone. The binder is contained in an amount of 0.5 to 25 parts by weight, and preferably 1 to 20 parts by weight, based on 100 parts by weight of the solid preparation of the invention.

The solid preparations of the invention can be produced by compressing a mixture of the crystals of the drug substance of the invention with excipients and disintegrating agents. For example, one method for the production includes mixing the crystals of the drug substance of the invention with the materials for the preparation by a suitable mixer, and directly compressing the mixture to tablets. Other methods include a dry granulating step to produce granules for tablets using dry granulating machines or roller compacters, and a wet granulating step to produce granules for tablets using water, ethanol and solutions containing binders when necessary.

There is no limitation to the dosage form of the solid preparation of the invention. An example is a tablet.

When the solid preparation is made in a form of a tablet, the tablet can be produced, for example, through granulating, sieving, mixing and tableting steps. Further, it is possible to coat the surface of the tablet by adding a coating step-to the production steps mentioned above.

Concrete examples of producing the tablet are as follows;

(1) Granulating Step

To a known granulating machine there are charged crystals of the drug substance of the invention, excipients, disintegrating agents and binders, and water is sprayed to the charged mixture, followed by granulating the mixture to obtain granules.

Otherwise, there may be charged crystals of the drug substance of the invention, excipients and disintegrating agents excluding binders, to a known granulating machine, and water in which binders are dissolved is sprayed to the charged mixture, followed by granulating the mixture to obtain granules.

In the former case, the granules at the end of spraying contains moisture (determined by the loss on drying method) in an amount of 17 to 26% by weight while in the latter case, the granules at the end of spraying contains moisture in an amount of about 10 to 16% by weight. That is, it is possible in the latter case to produce granules with a lesser amount of water, enabling to shorten the production time. The loss on drying method is carried out by drying powder under heat by emission of infrared rays and determining the percentage (%) of the moisture in the powder based on the weight change caused by the evaporation of water.

In the latter case, there is a tendency that the content ratio of drug substance at each particle size group (the content of drug substance in granules classified by the particle size) becomes constant.

(2) Sieving Step

The obtained granules are sieved through a desired sieve to remove coarse particles, for example, particles of 710 µm or larger.

(3) Mixing Step

The sieved granules are mixed with disintegrating agents and lubricants to obtain lubricated granules to be tableted.

(4) Tableting Step

The lubricated granules are tableted by a conventionally known, rotary tableting machine to obtain plain tablets.

In this step, conditions for the tableting may be those known to persons in the art. A preferred tableting pressure, for example, is 1,300 kgf/cm$^2$ or more and 5,200 kgf/cm$^2$ or less.

(5) Coating Step

A coating solution is prepared by dissolving a coating agent in water. Subsequently, the plain tablets are coated with the coating solution by a known coating machine to obtain the tablets of the invention.

The crystal of the drug substance of the invention is not limited to a particular particle size. Preferred average particle size is in the range from 3 µm to 50 µm (measured by an image analysis). When the size is less than 3 µm, the particle tends to be dispersed at weighing, or care should be taken at weighing and at the time the starting material is charged into a manufacturing equipment. However, the solid preparations of the invention can be produced even if the average particle size is out of the range. When the average particle size is over 50 µm, the produced solid preparations vary in the dissolution profile.

According to the invention, there are provided solid preparations that have less variation in the dissolution profile by using a single crystal form (the crystal form of the drug substance of the invention) and a method for producing the same. When the particle size of the crystal of the drug substance is controlled to be in a predetermined range, it is possible to provide solid preparations having a uniform dissolution profile and a method for producing the same.

According to the invention, it is possible to provide solid preparations having an improved content uniformity by using a single crystal form (the crystal form of the drug substance of the invention) and a method for producing the same. When the particle size of the crystal of the drug substance is controlled to be in a predetermined range, it is possible to provide solid preparations having a still more improved content uniformity (i.e., small CV valued preparations) and a method for producing the same.

According to the invention, it is possible to provide stable solid preparations wherein no transformation of effective ingredients is occurred during the process of formulating to tablets, etc., by using a single crystal form (the crystal form of the drug substance of the invention) and a method for producing the same.

The drug substance of the invention is preferably administered 1 to 3 times a day in an amount of 0.8 to 50 mg/day.

The solid preparation and a method for producing the same can be used for producing an inhibitor of xanthine oxidase, uric acid reducing agent, gout therapeutic agent or hyperuricemia therapeutic agent and a method for production of these agents.

The gout or hyperuricemia can be treated by administrating the solid preparations of the invention to patients.

That is, the invention provides a method for treating the gout or hyperuricemia, and a method for producing the therapeutic agent for treating the gout or hyperuricemia.

Further, the invention provides a method for administering a sole crystal form (crystal A) of 2-(3-cyano-4-isobutyloxyphenyl)-4-methyl-5-thiazolecarboxylic acid in a form of a solid preparation.

The invention is explained by reference to working examples. It should naturally be understood that the invention is not limited by these examples.

EXAMPLES

The stability, dissolution rate, solid $^{13}$N-NMR and $^{13}$C-NMR of each crystal form of drug substances (crystals A, B, C, D, E and G) of 2-(3-cyano-4-isobutyloxyphenyl)-4-methyl-5-thiazolecarboxylic acid were measured as reference examples.

The drug substances (crystals A, B, C, D, E and G) of 2-(3-cyano-4-isobutyloxyphenyl)-4-methyl-5-thiazolecarboxylic acid can be produced, for example, by the methods shown in International Publication WO 92/09279 and WO 99/65885.

Reference Example 1

Physical Stability

Each of the drug substances (crystals A, B, C, D, E and G) of 2-(3-cyano-4-isobutyloxyphenyl)-4-methyl-5-thiazolecarboxylic acid was tested in bottles with and without closure under the conditions of 40° C./75% RH. Any degradant was detected by a HPLC. Their transformation was detected by an X-ray powder diffraction pattern and by a thermal mass measurement method, and the 50% transform time was determined. The results are shown in Table 1. There was no degradant for all of the six crystal forms. Crystals A, C and G were stable even after storage for three months while transformation of crystals B, D and E was detected.

| | Analysis type | <50% Transform time> | |
| --- | --- | --- | --- |
| | | 40° C./75% RH without closure | 40° C./75% RH with closure |
| Crystal A | XRD | (Not changed) | (Not changed) |
| Crystal B | TG | 14 hours | 5 days |
| Crystal C | XRD | (Not changed) | (Not changed) |
| Crystal D | XRD | 0.25 hours | 17 days |
| Crystal E | XRD | 19 days | 55 days |
| Crystal G | XRD | (Not changed) | (Not changed) |

For the above HPLC, Model 2690 produced by Waters was adopted, using an ODS column with a measured wave length of 217 nm at a predetermined temperature around 40° C.

For the above X-ray powder diffraction, Model XRD-6000 of Shimadzu Corp. was used.

For the above heat mass measurement, Model TGA7, Pyris1 produced by Perkin Elmer was used at a temperature rising speed of 40° C./min.

Reference Example 2

Dissolution Rate

The dissolution rate was measured according to USP 24, <1087>Intrinsic Dissolution. Specifically, the measurement was carried out as follows:

50 mg each of crystals powdered lightly in an agate mortar was set between plates, and a pressure of 754 kgf/cm$^2$ was applied thereto for one minute to produce pellets. As the testing solution, 900 mL of the second fluid of the disintegration test of Japanese Pharmacopoeia was used and the test was carried out at 50 rpm using the dissolution apparatus produced by Vankel. Subsequently, the testing liquid was filtered through a filter and the resultant, used as the sample solution, was tested with respect to a standard solution by a spectrophotometry (wavelength of 317 nm). The results are shown in Table 2, in which the order of the dissolution rate of the six crystals is as follows: E>A>B>D>G>C.

| | Intrinsic rate (mg/cm$^2$/min) |
| --- | --- |
| Crystal A | 0.1434 |
| Crystal B | 0.1242 |
| Crystal C | 0.0694 |
| Crystal D | 0.1092 |
| Crystal E | 0.1874 |
| Crystal G | 0.0967 |

Reference Example 3

Solid NMR Data of Crystal Forms

The analysis of the drug substance contained in the preparations is limited only to solid NMR. Therefore, Crystals A, B, C, D, E and G of 2-(3-cyano-4-isobutyloxyphenyl)-4-methyl-5-thiazolecarboxylic acid was analyzed in advance by the solid NMR. The crystals show the following spectrums: Solid $^{15}$N-NMR Crystal A: Sharp peaks at 226 ppm, 228 ppm, 276 ppm and 282 ppm;

Crystal B: Broad peaks at 216 ppm, 222 ppm and 284 ppm;

Crystal C: Sharp single peaks at 210 ppm and 282 ppm;

Crystal D: Sharp single peaks at 229 ppm and 264 ppm;

Crystal E: Broad peaks at 223 ppm and 281 ppm;

Crystal G: Sharp single peaks at 216 ppm and 222 ppm, and a doublet peak at 283 ppm.

Solid $^{13}$C-NMR(specific peak at 20 ppm)

Crystal A: approximately equivalent doublet peaks;

Crystal B: non-equivalent doublet peaks;

Crystal C: approximately equivalent triplet peaks;

Crystal D: two single peaks;

Crystal E: Broad peaks;

Crystal G: non-equivalent triplet peaks.

In the following examples, each of the crystal forms was determined using the spectrum data described above.

Example 1

82.05 g of crystal A of 2-(3-cyano-4-isobutyloxyphenyl)-4-methyl-5-thiazolecarboxylic acid, 328.61 g of lactose (Pharmatose 200M, produced by DMV), 77.03 g of partly pregelatinized starch (PC-10, produced by Asahi Kasei Corp.), 12.31 g of hydroxypropyl cellulose (HPC-SL, produced by Nippon Soda Co.) were charged into a fluidized-bed granulator with agitator (New Marumerizer NQ-125, produced by Fuji Paudal) and were fluidized at a heater temperature of 60° C. with a air amount of 0.7 m$^3$/min. Subsequently, ion exchanged water was sprayed thereto at a spraying speed of 16 g/min, and dried at 60° C. to obtain granules containing about 12% by weight of the drug substance. The produced granules were sieved through a vibrating screen for removing particles having a size of 710 µm or greater to obtain sieved granules. 1,200 g of the sieved granules were mixed with 24.6 g of cross carmellose sodium (Ac-Di-Sol, produced by Asahi Kasei Corp.) and 6.15 g of magnesium stearate (produced by Sakai Chemical Ind.) in a cross rotary mixer (CM-10-S, produced by Tsukasa Ind.) to obtain the lubricated granules. The lubricated granules was tableted with a rotary type tableting machine (HT-P18, produced by Hata Tekkosho, tablet size: 7 mmφ, tableting pressure: 2,500 kgf/cm$^3$) The obtained preparations were analyzed by a solid $^{15}$N-NMR, with the result that there were sharp peaks at 226 ppm, 228 ppm, 276 ppm and 282 ppm. When the preparations were analyzed by a solid 13C-NMR,- the peak at 20 ppm was an approximately equivalent doublet peak and, accordingly, it was confirmed that crystal form of the drug substance in the preparations is all crystal A.

Comparative Example 1

Tablets were prepared by a method same as that of Example 1 except that crystal C of 2-(3-cyano-4-isobutyloxyphenyl)-4-methyl-5-thiazolecarboxylic acid was used. The obtained preparations were analyzed by a solid $^{15}$N-NMR, with the result that the peaks at 210 ppm and 282 ppm were broadened, an sharp peak was shown at 284 ppm and the peak at 20 ppm showed an broad peak when they were analyzed by a solid $^{13}$C-NMR. Accordingly, it was confirmed that crystals C and E were contained in the preparations.

Comparative Example 2

Tablets were prepared by a method same as that of Example 1 except that crystal B of 2-(3-cyano-4-isobutyloxyphenyl)-4-methyl-5-thiazolecarboxylic acid was used. The obtained preparations were analyzed by a solid $^{15}$N-NMR, with the result that the peaks at 216 ppm and 222 ppm were broadened, and the peak at 20 ppm showed an broad peak when they were analyzed by a solid $^{13}$C-NMR. Accordingly, it was confirmed that crystals B, G and E were contained in the preparations.

Comparative Example 3

Tablets were prepared by a method same as that of Example 1 except that crystal D of 2-(3-cyano-4-isobutyloxyphenyl)-4-methyl-5-thiazolecarboxylic acid was used. The obtained preparations were analyzed by a solid $^{15}$N-NMR, with the result that the peaks at 216 ppm, 222 ppm, 229 ppm and 264 ppm were broadened, and a broad peak was shown at 284 ppm. Further, the peak at 20 ppm showed a broad peak when they were analyzed by a solid $^{13}$C-NMR. Accordingly, it was confirmed that crystals D, G and E were contained in the preparations.

Comparative Example 4

Tablets were prepared by a method same as that of Example 1 except that crystal G of 2-(3-cyano-4-isobutyloxyphenyl)-4-methyl-5-thiazolecarboxylic acid was used. The obtained preparations were analyzed by a solid $^{15}$N-NMR, with the result that the peaks at 216 ppm and 222 ppm were broadened, and a broad peak was shown at 284 ppm. Further, the peak at 20 ppm showed a broad peak when the preparations were analyzed by a solid $^{13}$C-NMR. Accordingly, it was confirmed that crystals G and E were contained in the preparations.

Example 2

The tablets prepared by the method shown in Example 1 were tested for six months under the conditions of 40° C./75% RH. Then the uniformity of content (the ratio of the amount of the drug substance contained in actual tablets to the amount charged) and the crystal form of the tablets just after produced and after six months storage were studied. The content in tablets just after produced was 99.72% and the CV value (coefficient of variation) showing the variation in content was 1.37%. The content after storage for six months was 99.5%, and the CV value showing the variation in content is 1.55%, which demonstrates a superior uniformity. The crystal form of the tablets was analyzed by a solid $^{15}$N-NMR, just as the case with immediately after produced. The result showed that sharp peaks were shown at 226 ppm, 228 ppm, 276 ppm and 282 ppm. Further, the results of the analysis by a solid=$^{13}$C-NMR showed that the peak at 20 ppm was an approximately equivalent doublet peak and, accordingly, it was confirmed that the preparations contains crystal A.

Comparative Example 5

Tablets prepared in Comparative Examples 1 through 4 were tested for six months under the conditions of 40° C./75% RH, and the uniformity in content of the drug substance in tablets and the crystal form of the tablets just after produced and after six months were checked.

The content of the drug substance in tablets just after produced in Comparative Example 1 was 100.37% and the CV value (coefficient of variation) showing the variation in content was 1.11%. The content after storage for six months is 99.5% or greater, and the variation in content shown by a CV value showed an improved value of 1.68%. But it was confirmed that the preparations comprise crystals C and E according to the solid NMR. The analysis of preparations after storage showed that a part of crystal E was transformed to crystal G. For the preparations produced in Comparative Example 2, the content in tablets immediately after produced was 99.75% and the CV value showing the variation in content was 1.11%. The content after storage was 99.5% or greater and the variation expressed by a CV value showed an improved uniformity of 1.90%. But it was confirmed that the preparations comprise crystals B, G and E according to the solid NMR. Further, it was confirmed that the ratio of crystal E was reduced and that of crystal G was increased after storage For the preparations produced in Comparative Example 3, the content in tablets immediately after produced was 100.01% and the variation shown by a CV value was 1.39%. The content in tablets after storage maintained 99.5% or more and the CV value showed an improved uniformity of 1.54%. But it was confirmed that the preparations comprise crystals D, G and E according to the solid NMR. Further, it was confirmed that the ratio of crystal E was reduced and that of crystal G was increased after storage.

For the preparations produced in Comparative Example 4, the content in tablets immediately after produced was 93.5% and the variation shown by a CV value was 4.5%, which facts show that the content of the drug substance contained in tablets to the amount charged is very low and that there is a considerable variation. Therefore, the tablets did not reach the level of being brought to a market and, thus, no stability test has been carried out.

Example 3

The tablets prepared by the method shown in Example 1 were tested for six months under the conditions of 40° C./75% RH. Then the dissolution profiles of the tablets just after produced and after six months were compared. The dissolution test was carried out by a Paddle method using a McIlvaine buffer solution of pH 5.5 as a testing solution. Three lots (n=3), i.e., 9 test examples in total, were produced by a same method and were tested. The results are shown in Table 3. It was confirmed, as shown in Table 3, that there is little variation or difference in dissolution ratio between points and uniform dissolution profiles are maintained even after storage of six months.

TABLE 3

| Dissolution time (min) | Immediately after produced | | Six months after storage | |
|---|---|---|---|---|
| | Average dissolution ratio (%) | CV value (%) | Average dissolution ratio (%) | CV value (%) |
| 15 | 69.8 | 2.8 | 71.6 | 3.1 |
| 60 | 90.1 | 2.8 | 91.7 | 2.9 |

Comparative Example 6

For the preparations produced in Comparative Examples 1 through 3 comparisons were made between the dissolution profiles of those immediately after produced and those having been tested for six months under the conditions of 40° C./75% RH. The dissolution test was carried out by a Paddle method using a McIlvaine buffer solution of pH 5.5 as a testing solution. Three lots (n=3), i.e., 9 test examples in total, were produced by a same method and were tested. The results are shown in Tables 4 through 6.

The preparations of Comparative Example 3 after storage showed a slower dissolution profile than those immediately after produced, as shown in Table 4. Further, there is some variation or difference in dissolution ratio between points for the preparations after storage. This is thought to be caused by that crystal E was transformed, by the storage, into crystal G having low solubility. The variation or difference in dissolution ratio between points are thought to be caused by that the ratio of crystals C and E is uneven between lots and that the transformed amount of crystal G from crystal E is not uniform.

The preparations of Comparative Example 2 after storage showed a slower dissolution profile than those immediately after produced, as shown in Table 5. Further, there is some variation or difference in dissolution ratio between points for the preparations after storage. This is thought to be caused by that crystals B and E were transformed, by the storage, into crystal G having low solubility. The variation or difference in dissolution ratio between points are thought to be caused by that the ratio of crystals B and E is uneven between lots and that the transformed amount of crystal G from crystals B and E is not uniform.

The preparations of Comparative Example 3 after storage showed a slower dissolution profile than those immediately after produced, as shown in Table 6. Further, there is some variation or difference in dissolution ratio between points for the preparations after storage. This is thought to be caused by that crystals D and E were transformed, by the storage, into crystal G having low solubility. The variation or difference in dissolution ratio between points are thought to be caused by that the ratio of crystals D and E is uneven between lots and that the transformed amount of crystal G from crystals D and E is not uniform.

TABLE 4

Dissolution Profile of the Preparations Produced by Comparative Example 1

| Dissolution time (min) | Immediately after produced | | Six months after storage | |
|---|---|---|---|---|
| | Average dissolution ratio (%) | CV value (%) | Average dissolution ratio (%) | CV value (%) |
| 15 | 54.8 | 18.5 | 46.2 | 19.8 |
| 60 | 75.1 | 15.7 | 62.1 | 16.4 |

TABLE 5

Dissolution Profile of the Preparations Produced by Comparative Example 2

| Dissolution time (min) | Immediately after produced | | Six months after storage | |
|---|---|---|---|---|
| | Average dissolution ratio (%) | CV value (%) | Average dissolution ratio (%) | CV value (%) |
| 15 | 55.1 | 10.8 | 48.3 | 20.4 |
| 60 | 72.1 | 18.4 | 63.5 | 30.2 |

TABLE 6

Dissolution Profile of the Preparations Produced by Comparative Dissolution Profile of the Preparations Produced by Comparative Example 3

| Dissolution time (min) | Immediately after produced | | Six months after storage | |
|---|---|---|---|---|
| | Average dissolution ratio (%) | CV value (%) | Average dissolution ratio (%) | CV value (%) |
| 15 | 53.3 | 18.1 | 47.3 | 19.4 |
| 60 | 60.4 | 10.9 | 56.1 | 22.0 |

Example 4

Plain tablets were prepared by the method same as that of Example 1 except that particles (Particles 1~4) shown in Table 7, with crystal A and with four different kinds of average particle sizes, were used as 2-(3-cyano-4-isobutyloxyphenyl)-4-methyl-5-thiazolecarboxylic acid. The obtained plain tablets were coated with coating liquid comprising purified water, polyethylene glycol and hydroxypropylmethyl cellulose by a coating machine (High Coater HCT-30, Freund Ind.).

Figure 1:
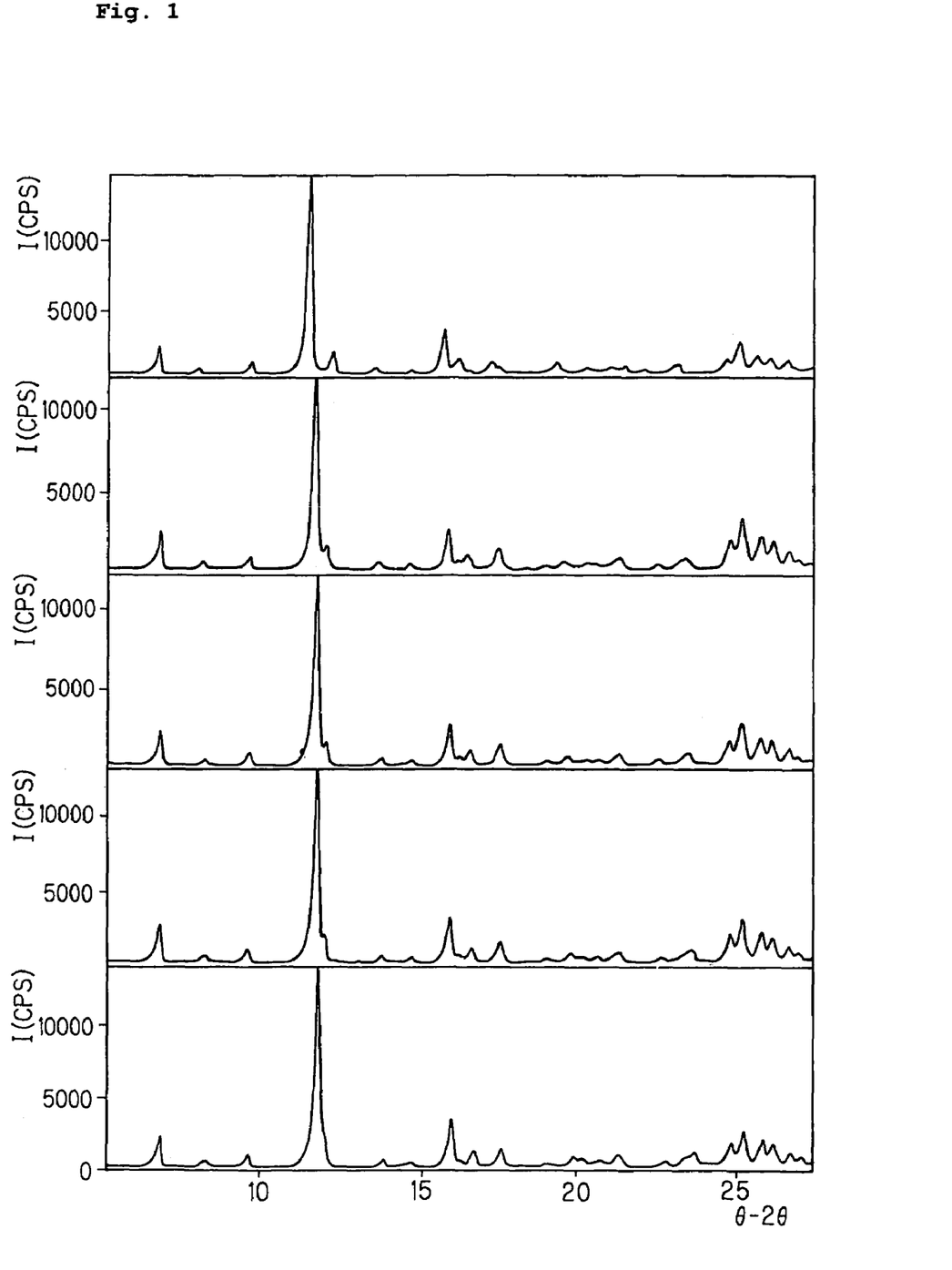
FIG. 1 is an X-ray powder diffraction pattern showing the transformation of crystal B in Reference Example 1.
Figure 2:
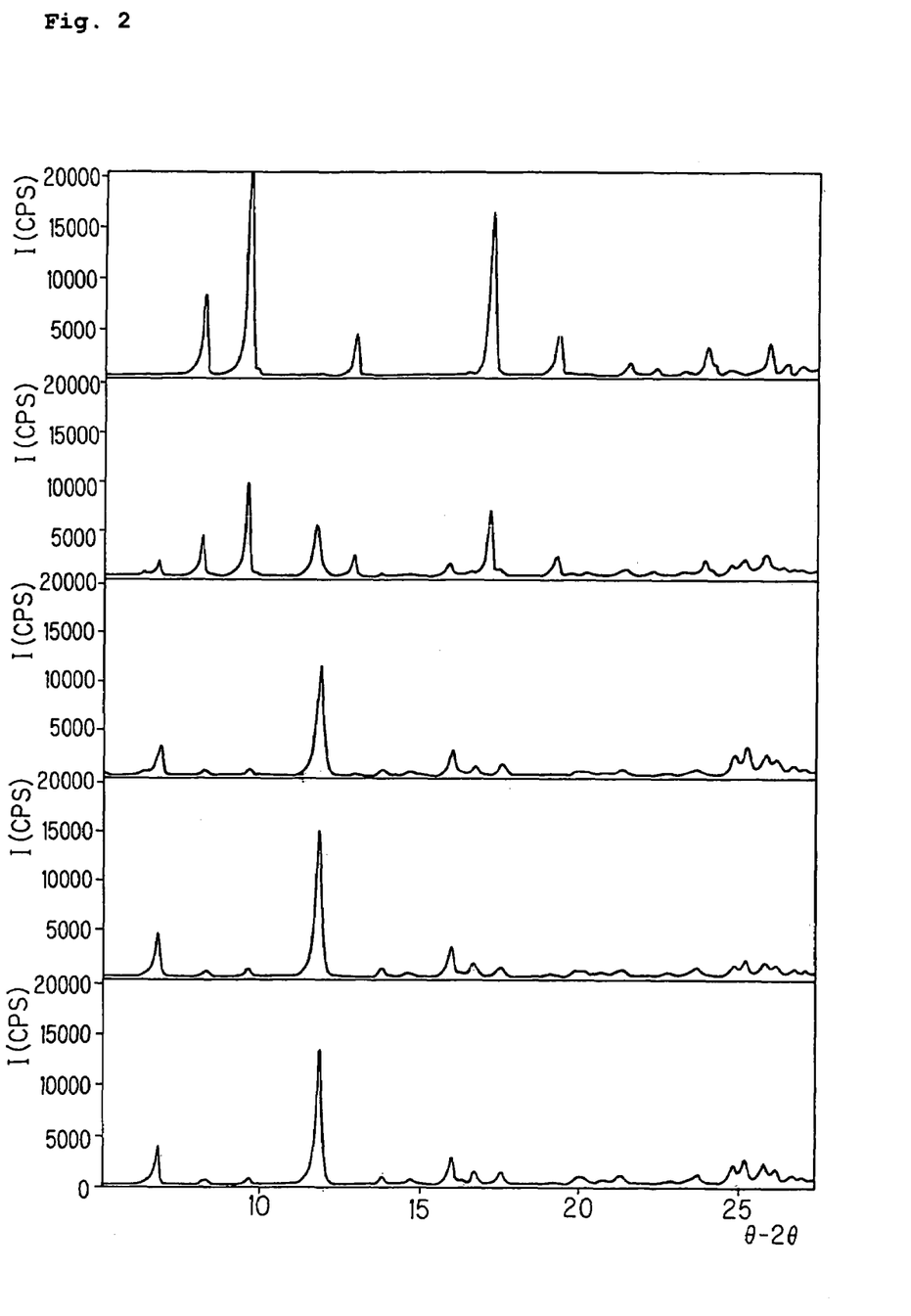
FIG. 2 is an X-ray powder diffraction pattern showing the transformation of crystal D in Reference Example 1.
Figure 3:
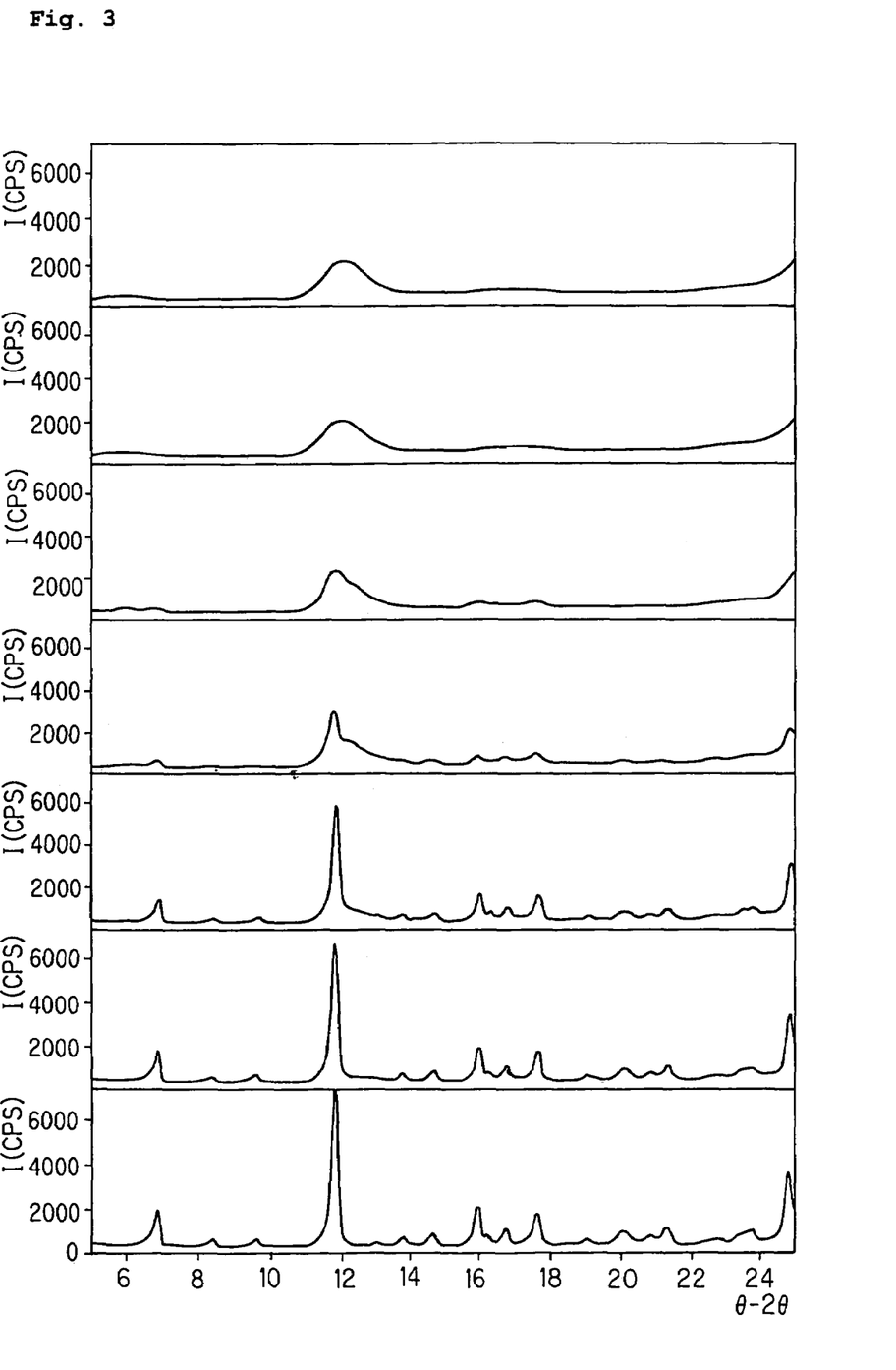
FIG. 3 is an X-ray powder diffraction pattern showing the transformation of crystal E in Reference Example 1.
Figure 4:
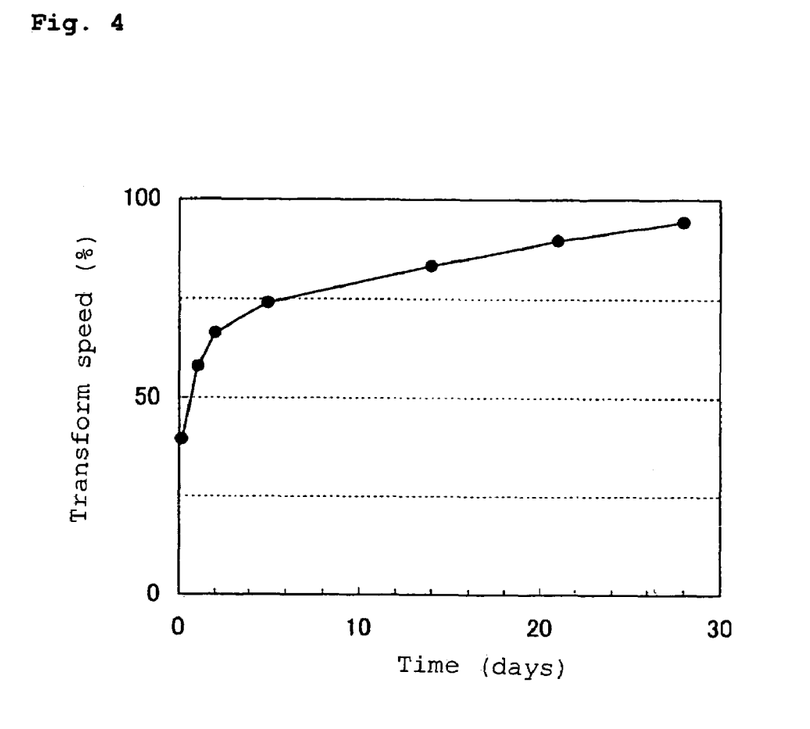
FIG. 4 is a data showing the transformation speed of crystal B in Reference Example 1 (unsealed state at 40° C./75% RH).
Figure 5:
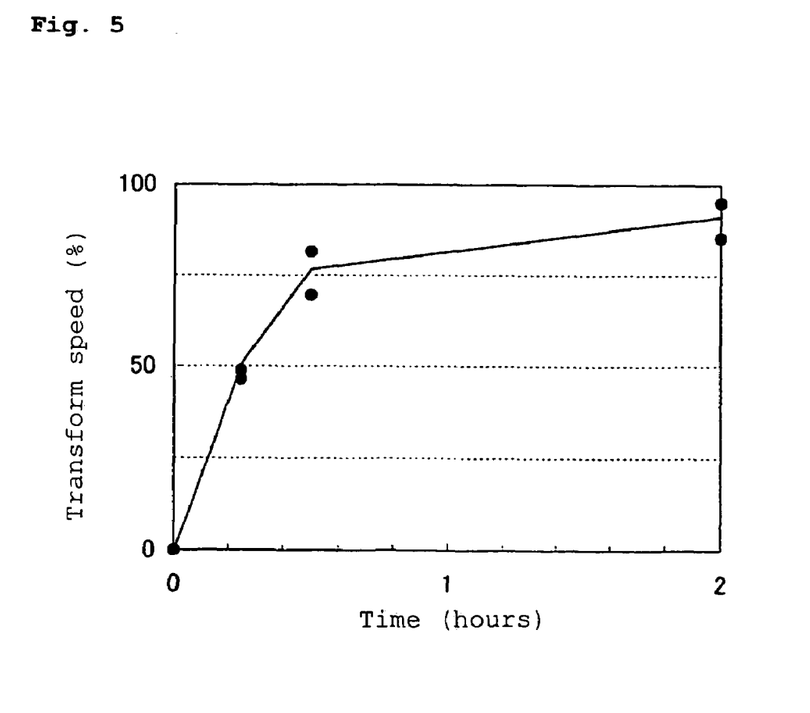
FIG. 5 is a data showing the transformation speed of crystal D in Reference Example 1 (unsealed at 40° C./75% RH).
Figure 6:
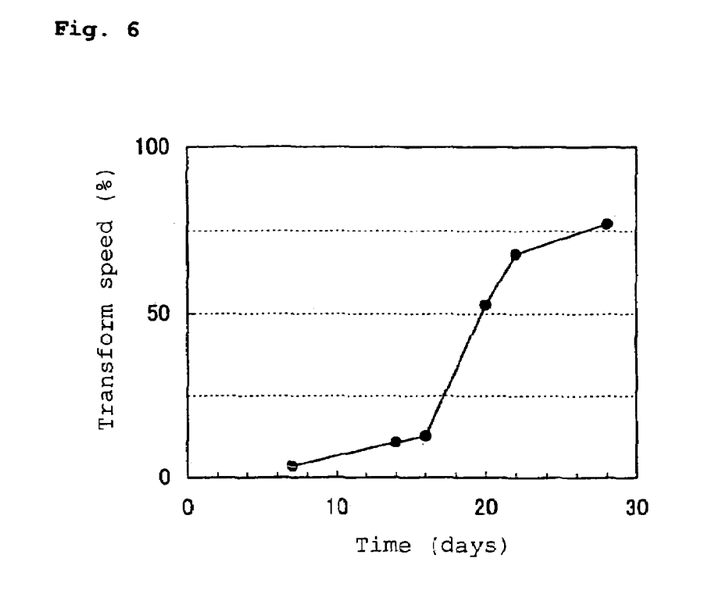
FIG. 6 is a data showing the transformation speed of crystal E in Reference example 1 (unsealed at 40° C./75% RH).
Figure 7:
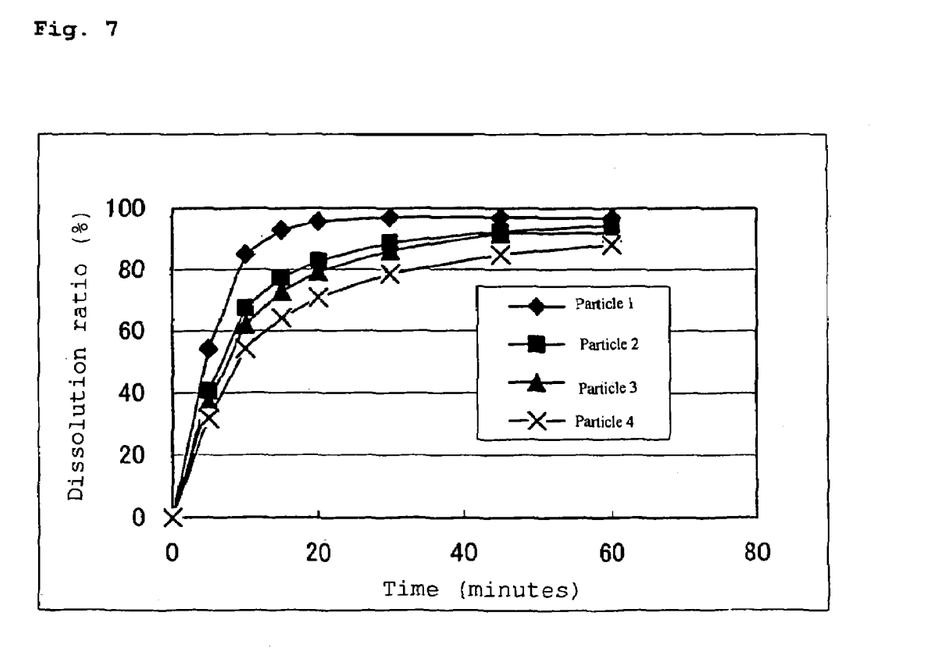
FIG. 7 shows dissolution profiles of tablets containing crystal A (particles 1 to 4) in Example 4 each having a different average particle size.

Dissolution tests were carried out for the four types of the obtained coated tablets by a Paddle method using a McIlvaine buffer solution with pH 5.5, as a testing liquid. The results are shown in Table 7.

TABLE 7

| | | | Pulverized particle size ($\mu m$)[1] | |
|---|---|---|---|---|
| | Pulverizer | Pulverizing conditions | Average particle diameter | 95% cumulative diameter |
| Particle 1 | Jet mill (Dalton, PJM-100SP) | Feeding speed: 5.0 kg/hr Pulverizing pressure: 0.65 MPa | 3.5 | 5.6 |
| Particle 2 | Sample mill (Dalton, KII WG-1) | Screen 2.0 mmΦ 12,000 rpm | 12.9 | 29.5 |
| Particle 3 | Impact mill (Dalton, DS-2) | Screen 1.0 mmΦ 6,120 rpm | 26.2 | 74.7 |
| Particle 4 | Power mill (Dalton, P-3) | Screen 2 Hmm 4,000 rpm | 48.6 | 140.8 |

[1]Results measured by an image analysis Measuring instruments (image analysis system, digital camera for microscope and biological microscope)

The invention claimed is:

1. A tablet comprising crystal A of 2-(3-cyano-4-isobutyloxyphenyl)-4-methyl-5-thiazolecarboxylic acid with an X-ray powder diffraction pattern having specific peaks at a reflection angle 2θ, of 6.62°, 7.18°, 12.80°, 13.26°, 16.48°, 19.58°, 21.92°, 22.68°, 25.84°, 26.70°, 29.16° and 36.70°, an excipient, and a disintegrating agent, wherein the average particle diameter of the crystal A is from 12.9 μm to 26.2 μm.

2. The tablet according to claim 1, wherein the tablet is prepared by a wet granulating method.

3. The tablet according to claim 1 or 2, wherein said excipient is one or more selected from the group consisting of lactose and partly pregelatinized starch.

4. The tablet according to claim 1 or 2, further comprising hydroxypropyl cellulose as a binder.

5. The tablet according to claim 1 or 2, wherein the tablet is coated with polyethylene glycol.

6. A method for producing the tablet according to claim 2 comprising combining said crystal A of 2-(3-cyano-4-isobutyloxyphenyl)-4-methyl-5-thiazolecarboxylic acid with an X-ray powder diffraction pattern having specific peaks at a reflection angle 2θ, of 6.62°, 7.18°, 12.80°, 13.26°, 16.48°, 19.58°, 21.92°, 22.68°, 25.84°, 26.70°, 29.16° and 36.70°, an excipient, and a disintegrating agent, wherein the average particle diameter of the crystal A is from 12.9 μm to 26.2 μm.

7. The method for producing a tablet according to claim 6, comprising a step of wet granulating.

8. The method for producing a tablet according to claim 6 or 7, wherein said excipient is one or more selected from the group consisting of lactose and partly pregelatinized starch.

9. The method for producing a tablet according to claim 6 or 7, wherein hydroxypropyl cellulose is added as a binder.

10. The method for producing a tablet according to claim 6 or 7, comprising a step of coating the tablet with polyethylene glycol.

* * * * *